United States Patent
Hoelzer et al.

(10) Patent No.: US 11,630,995 B2
(45) Date of Patent: Apr. 18, 2023

(54) CHARACTERIZATION OF AMOUNT OF TRAINING FOR AN INPUT TO A MACHINE-LEARNED NETWORK

(71) Applicant: Siemens Healthcare GmbH, Erlangen (DE)

(72) Inventors: Philipp Hoelzer, Baltimore, MD (US); Sasa Grbic, Plainsboro, NJ (US); Daguang Xu, Princeton, NJ (US)

(73) Assignee: Siemens Healthcare GmbH, Erlangen (DE)

( * ) Notice: Subject to any disclaimer, the term of this patent is extended or adjusted under 35 U.S.C. 154(b) by 1339 days.

(21) Appl. No.: 16/012,151

(22) Filed: Jun. 19, 2018

(65) Prior Publication Data

US 2019/0385738 A1 Dec. 19, 2019

(51) Int. Cl.
*G06F 18/2411* (2023.01)
*G06N 3/08* (2023.01)
(Continued)

(52) U.S. Cl.
CPC .............. *G06N 3/08* (2013.01); *G06F 18/22* (2023.01); *G06F 18/2411* (2023.01);
(Continued)

(58) Field of Classification Search
CPC ........ G16H 50/20; G16H 50/00; G16H 50/70; G16H 30/40; G06K 9/6215; G06K 9/6269;
(Continued)

(56) References Cited

U.S. PATENT DOCUMENTS 10,282,588 B2  5/2019 Comaniciu et al.
2016/0140300 A1* 5/2016 Purdie .................... G16H 10/60
                                                                 705/2
(Continued)

FOREIGN PATENT DOCUMENTS

CN         107492090 A    12/2017

OTHER PUBLICATIONS

Rizwan et al, WR-SVM Model based on the Margin Radius Approach for . . . Support Vector Machine Classification, 2021, Appl Sci, 11(4657) pp. 1-21. (Year: 2021).*

(Continued)

*Primary Examiner* — Matthew C Bella
*Assistant Examiner* — Kathleen M Broughton

(57) ABSTRACT

The user is to be informed of the reliability of the machine-learned model based on the current input relative to the training data used to train the model or the model itself. In a medical situation, the data for a current patient is compared to the training data used to train a prediction model and/or to a decision function of the prediction model. The comparison indicates the training content relative to the current patient, so provides a user with information on the reliability of the prediction for the current situation. The indication deals with the variation of the data of the current patient from the training data or relative to the prediction model, allowing the user to see how well trained the predication model is relative to the current patient. This indication is in addition to any global confidence output through application of the prediction model to the data of the current patient.

15 Claims, 2 Drawing Sheets

(51) Int. Cl.
  *G16H 50/20*    (2018.01)
  *G16H 30/40*    (2018.01)
  *G06N 3/02*     (2006.01)
  *G16H 50/00*    (2018.01)
  *G16H 50/70*    (2018.01)
  *G06V 10/70*    (2022.01)
  *G06F 18/22*    (2023.01)
  *G06F 18/2415*  (2023.01)
  *G06V 10/772*   (2022.01)
  *G06V 10/778*   (2022.01)
  *G06V 10/94*    (2022.01)

(52) U.S. Cl.
  CPC ......... *G06F 18/24155* (2023.01); *G06N 3/02* (2013.01); *G06V 10/70* (2022.01); *G06V 10/772* (2022.01); *G06V 10/7796* (2022.01); *G06V 10/945* (2022.01); *G16H 30/40* (2018.01); *G16H 50/00* (2018.01); *G16H 50/20* (2018.01); *G16H 50/70* (2018.01); *G06V 2201/03* (2022.01)

(58) Field of Classification Search
  CPC ...... G06K 9/6278; G06K 9/6285; G06N 3/02; G06N 3/08; G06N 5/003; G06V 10/70; G06V 10/772; G06V 10/7796; G06V 10/945; G06V 2201/03
  See application file for complete search history.

(56) References Cited

U.S. PATENT DOCUMENTS

2017/0018075 A1* 1/2017 Middlebrooks .... G06V 10/7784
2017/0177812 A1* 6/2017 Sjölund ................. G16H 20/40
2018/0043182 A1* 2/2018 Wu ..................... A61N 5/1039

OTHER PUBLICATIONS

Mourao-Miranda et al (Individualized prediction of illness . . . Support Vector Machine MRI study, 2011, Psych Med 42(5): 1037-47. (Year: 2011).*

Kukar, Matjaž. "Estimating confidence values of individual predictions by their typicalness and reliability." Proceedings of the 16th European Conference on Artificial Intelligence. IOS Press, 2004.

* cited by examiner

CHARACTERIZATION OF AMOUNT OF TRAINING FOR AN INPUT TO A MACHINE-LEARNED NETWORK

BACKGROUND

The present embodiments relate to machine learning. Machine learning algorithms have shown great promise for the computer-aided diagnosis of medical images. The capability of the algorithm to generalize, categorize, and/or distinguish different clinical findings depends on the quality and quantity of the training data. However, different diseases or other clinical indications occur with different prevalence, resulting in different availability of training data for different situations. For application of a machine-learned model, where the training data may be different compared to the data for a particular patient, unrealistic looking results may be presented to the user. For example, in the case of organ segmentation, a machine-learned segmentation may produce unrealistic looking organ contours where insufficient training data with similar organ structure was used in training. This causes a break in the trust between the user and the application.

To overcome this problem, more training data may be gathered. However, sufficient training data may be unavailable for some situations. Another approach is to apply a rule-based or manually programmed application, but such applications have limited abilities to generalize to some patient situations.

SUMMARY

By way of introduction, the preferred embodiments described below include methods, systems, instructions, and computer readable media for characterizing an amount of training. The user is to be informed of the reliability of the machine-learned model based on the current input relative to the training data used to train the model or the model itself. In a medical situation, the data for a current patient is compared to the training data used to train a prediction model and/or to a decision function of the prediction model. The comparison indicates the training content relative to the current patient, so provides a user with information on the reliability of the prediction for the current situation. The indication deals with the variation of the data of the current patient from the training data or relative to the prediction model, allowing the user to see how well trained the prediction model is relative to the current patient. This indication is in addition to any global confidence output through application of the prediction model to the data of the current patient.

In a first aspect, a method is provided for characterizing an amount of training in a medical system. A medical imaging scanner scans a patient. Values for input features of a machine-learned network are applied to the machine-learned network. The values are for the patient and at least one of the values is from the scanning. The application results in an output by the machine-learned network. A relative position or positions of the values for the input features of the patient to (a) values of the input features for training data used to train the machine-learned network and/or (b) a decision function of the machine-learned network are determined. An image of the output by the machine-learned network and the amount of training relative to the values for the patient is displayed. The amount of training is a function of the relative position.

In a second aspect, a system is provided for characterizing an amount of training of a machine-learned prediction model relative to an input sample. A memory is provided for storing training data of values for parameters, the input sample of values for the parameters, and a machine-learned prediction model. A processor is configured to output from the machine-learned prediction model in response to input of the input sample of the values for the parameters and to determine the amount of the training of the machine-learned prediction model from a comparison of the values for the parameters for the input sample to the values for the parameters of the training data and/or to a decision function of the machine-learned prediction model. A display is configured to output an image of the amount of the training of the machine-learned prediction model relative to the input sample.

In a third aspect, a method characterizing an amount of training is provided. Training data is mapped in a feature space with each sample of the training data labeled by a ground truth. An input for a current sample not in the training data is mapped in the feature space. A metric of a distance of the input for the current sample from the training data in the feature space is determined. The metric is displayed as the amount of training for a machine-learned prediction model trained with the training data.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

To assist a user of a machine-learned prediction model in understanding the reliability of a given prediction, a confidence metric is provided. For machine learning algorithms, the amount of relevant training is characterized by the metric. The metric may measure a distance of a current input feature vector from the feature vectors of the training data. The metric may measure a distance of the current input feature vector from a decision function in the features space of the training data. The metric may measure an amount of wrongly categorized training data relative to the current input feature vector. The metric may measure a density of training data points in close vicinity to the current sample.

Figure 1:
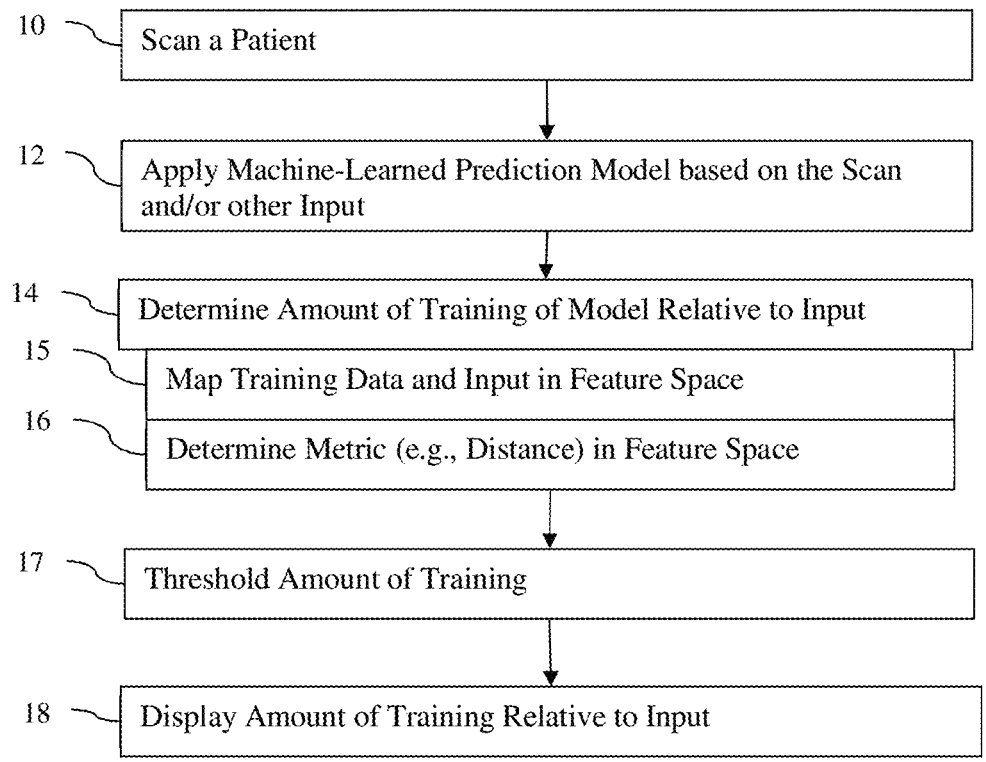
FIG. 1 is one embodiment of a method for characterizing an amount of training of a prediction model relative to a current input.

FIG. 1 shows one embodiment of a method for characterizing an amount of training relative to specific input. Rather than relying on any global indication of confidence output from a machine-learned prediction model itself, the input feature vector used for prediction is compared to a decision function of the prediction model or the training data to indicate the amount of training or how well the prediction model was trained relative to the specific input feature vector. If the current sample is far away from the decision function and resides well in one classified region, a lower number of training data points might be sufficient. Conversely, if the current sample lies close to the decision function, then a higher local density of neighboring training data points might be needed to ensure a classification with high confidence.

In the examples below, the amount of training relative to medical imaging or in a medical system is characterized. Non-medical embodiments may be provided, such as for power distribution, image processing, industrial control, or other environments where a machine-learned prediction model is used.

Figure 4:
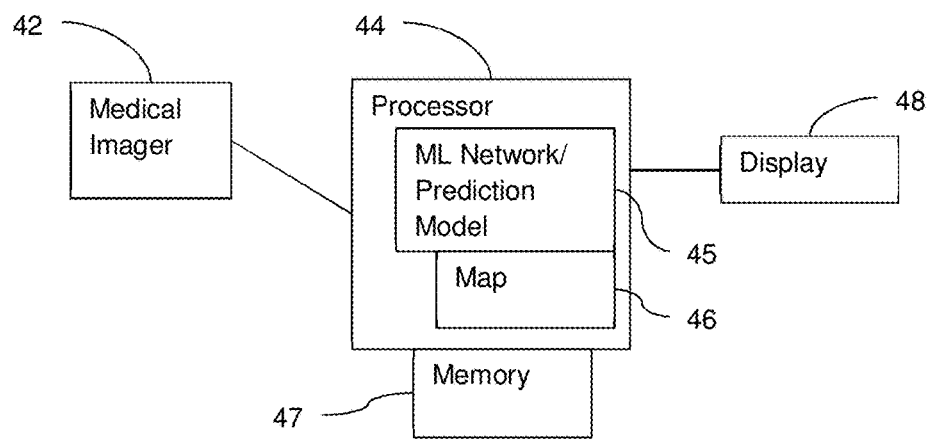
FIG. 4 is a block diagram of one embodiment of a system for characterizing an amount of training of a machine-learned prediction model relative to an input sample.

The method is implemented by the system of FIG. 4 or another system. For example, the method is implemented by a computer, server, medical imager, or other processor. A medical imager scans in act 10. An image or other processor (e.g., server, computer, or processor of the medical imager) applies in act 12, determines in act 14, thresholds in act 17, and outputs to a display device, which displays in act 18. Different devices may be used.

Additional, different, or fewer acts may be provided. For example, the scan of act 10 is not provided, such as where non-imaging data is used without imaging data or in non-medical embodiments. As another example, the output is to a memory (e.g., medical record) and/or computer network rather than a display in act 18. In yet another example, act 17 is not used where the output is of the metric itself without any thresholding. As yet another example, act 12 is not provided, such as where the amount of training relative to the input is too low or indicates poor prediction is likely.

The acts are performed in the order shown (e.g., top to bottom or numerical) or other orders. For example, act 17 may be applied after act 18 where the metric is displayed, and the displayed metric is then thresholded to then indicate a level of concern relative to the amount of training. As another example, act 12 may be performed after act 18 or not at all.

In act 10, a medical imaging scanner scans a patient. The medical imaging scanner is any medical imager, such as a computed tomography (CT), magnetic resonance (MR), C-arm, ultrasound, x-ray, photoacoustic tomography, optical camera, depth camera, diffuse optical imaging, magnetic particle imaging, optical coherence tomography, nuclear medicine, or other medical scanner for scanning the interior and/or exterior of a patient.

The patient is scanned along a plane or in a volume. Energy, such as x-rays, electromagnetic pulses, acoustic, or other, may be transmitted into the patient. The energy as passed through the patient is detected, and/or a response to the energy is received or detected from the patient. Alternatively, the scan measures emissions from within the patient. The detected response, energy, or emissions are scan data.

The scan data may be processed as part of the scan. For example, reconstruction is applied. The reconstruction may determine response of the patient by locations within the patient, such as for voxels or pixels in a volume or plane of the patient. For MR, k-space data is reconstructed with a Fourier transform. For CT, projection images from different directions relative to the patient are reconstructed by computed tomography. For nuclear medicine, detected emissions along lines of response are reconstructed by tomography.

Non-scan data may be obtained. Data from other sensors, lab results, history, findings, or other information are obtained by receipt or look-up. The imaging or scan data with or without other data is obtained. Alternatively, other data without imaging or scan data is obtained. The data for an input feature vector of a machine-learned model is acquired.

In act 12, a processor applies values for input features of a machine-learned network to the machine-learned network. The input feature vector obtained or derived from the information obtained in act 10 is input to the machine-learned network. In the medical example, values of features for a patient, such as derived from scan data (e.g., image processing) or the scan data itself (e.g., image), are input. Values for features from sources other than scanning may be input.

The machine-learned network is any prediction model trained with a machine learning algorithm. Any type of machine learning and corresponding machine-learned network may be used. For example, deep learning with a neural network architecture, such as a convolutional neural network, deep belief network, deep residual learning, reinforcement learning, recurrent neural network, recursive neural network, feature pyramid network, Siamese network, and/or generative adversarial network, may be used. Probabilistic boosting tree, support vector machine, Bayesian classifier, k-means clustering, decision trees, inductive programming, or other networks and corresponding training may be used.

The prediction model is to perform any image or other processing function. The prediction model is trained to provide a clinical finding. For example, the prediction model is trained to detect an object (e.g., organ or tumor), segment an object, register different scans, simulate function (e.g., cardiac flow), fuse information from different scans, determine diagnosis, determine prognosis, recommend treatment, multi-material decomposition, and/or other operation. In one embodiment, the prediction model outputs an image analysis (e.g., detection or segmentation) in response to input of the scan data (e.g., input of one or more images from medical imaging of the patient).

The prediction model is trained using training data. Many samples, such as hundreds or thousands of samples of input data and known or ground truth output data, are collected to train. The machine learning algorithm is applied to train the prediction model to output based on an unseen input feature vector. The same type of data as the training samples but without the ground truth may be input to the trained prediction model, resulting in output of the predicted response (e.g., output a segmentation or detected object in response to input of an image for a patient). The training data and a learning-based evaluation algorithm of new input data are used to create a prediction model. The prediction model may then be applied to unseen inputs, such as scans or features from a scan for other patients.

Figure 2:
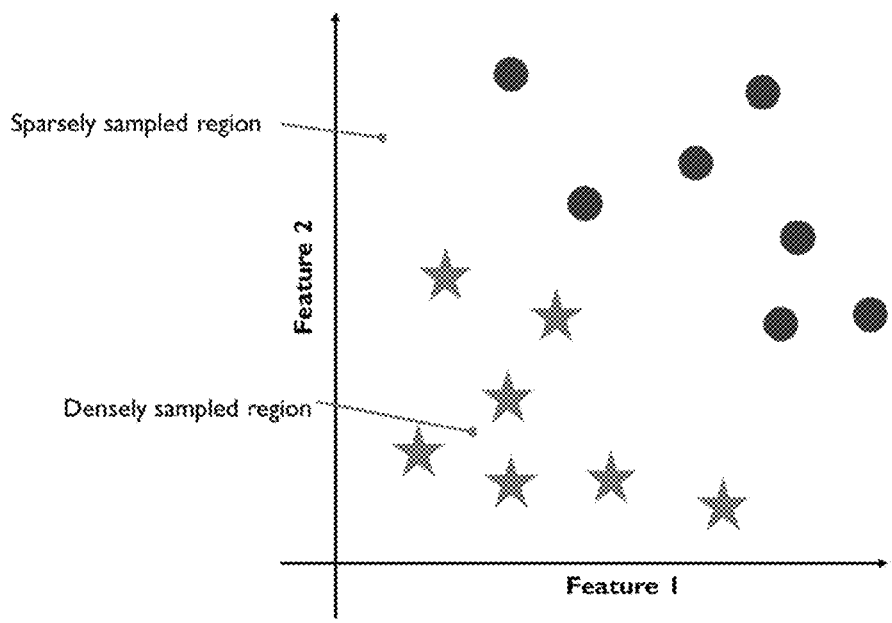
FIG. 2 illustrates example mapping of training data and a current sample.

FIG. 2 shows an example representation of the training data. In this simplified example, there are two features (e.g., size and shape) used to predict a binary output (e.g., benign or malignant tumor). The circles represent benign, and the stars represent malignant. Each circle and star represents one sample (e.g., 14 samples total) of training data. Many more features, ground truth outputs, and/or samples may be provided. Example features or parameters include scan data (e.g., images), features from the scan data (e.g., Haar wavelets), image resolution, dose, contrast, reconstruction kernel used, patient age, patient gender, patient BMI, patient height, texture metrics such as mean intensity, maximum intensity, minimum intensity, uniformity, entropy (irregularity of gray-level distribution), standard deviation of the gray level histogram distribution, skewness (asymmetry of the histogram), kurtosis (flatness of the histogram) & entropy (randomness of matrix), energy/angular second moment (pixel repetition/orderliness and measures of co-occurrence matrix), dissimilarity (measurement of how different each element in the matrix is), correlation (measurement of gray tone linear dependencies), run-length matrix (texture in a specific direction), neighborhood gray-tone difference matrices (spatial relationship among three or more pixels), contrast (number of local variations within image), coarseness (measurement of edge density), busyness (measurement of spatial rate of gray-level change) and/or other parameters.

As shown in FIG. 2, some regions of the feature (e.g., sample parameter) space of the graph include more dense representation from the samples. Some regions of the features space have more sparse representation. A prediction model trained from this training data may be better at predicting the output where the unseen input feature vector is in the more densely sampled region than the sparsely sampled region. Rather than merely providing an output regardless of the density at the unseen input, the user may be provided with information about the amount of training data similar to the unseen input to better judge likely reliability of the output.

The prediction model may output a probability. This global confidence score reflects various aspects of the prediction, including how separable the training data is with regards to the ground truth. As a result, the global confidence less directly or not at all represents the amount of training with respect to the current (unseen) input sample.

The trained network or prediction model is stored in a memory. The trained artificial intelligence (i.e., machine-learned network) is stored. The result of the training is a matrix or other prediction model (e.g., filter kernels, node links, and/or weights). The prediction model represents the learned knowledge through machine training.

Once trained, the machine-learned network is applied by a machine, such as a computer, processor, or server. The machine uses input data for a patient (i.e., scan data, clinical information, results from image processing, patient information, and/or information derived therefrom) and the machine-learned network to generate an output specific to that patient. The application of the values in the input feature vector (e.g., input of the image or other scan data) to the machine-learned network results in an output by the network.

In some situations, the output may not be accurate. Where the user can view the results and tell, then the user knows to attempt another approach. The lack of accuracy may not be apparent to the user or may require precise study over time not allowed for the user. The amount of training with respect to the input feature vector for the patient may be characterized to provide the user with more information on the reliability of the output by the prediction model.

In act 14, the processor determines a relative position of the values for the input features of the patient to the training data. The training data may be represented by itself and/or the decision function of the machine-learned network of the prediction model. The relative position of the values for a current input to (a) the values of the inputs for the training data used to train the prediction model and/or (b) a decision function of the machine-learned network is determined. The relative position indicates a confidence level of the output of the prediction model.

The relative position may be a density, a distance, or other measure of similarity to a closest, a group of closest, other sub-set, or all the training data or decision function. For example, a distance from M closest training data samples to a sample for the current patient is measured. As another example, a density within a given region or % of the total feature space centered on the sample for the current patient is measured.

Acts 15 and 16 represent one embodiment for determining the amount of training of the prediction model relative to a current input. Other approaches may be used, such as using a search or look-up instead of mapping. In another embodiment, a machine-learned network is used to determine the amount based on the training data or decision function and the current input feature vector.

In act 15, the processor maps the training data in a feature space with each sample of the training data labeled by a ground truth. This mapping may be performed prior to or after training the prediction model. The training data is mapped in parameter space by retaining the output labels. FIG. 2 illustrates one embodiment of the mapping. The mapping may be an N dimensional representation where N is an integer representing the number of different features or parameters. The map may be formatted in any way, such as a list.

The mapping may be of the decision function instead of or in addition to the samples of the training data. The machine learning creates a decision function. The resulting prediction model may be used to map out the decision function. In one embodiment, a regular search of value combinations of the input feature vector is used to determine the locations in the feature space that distinguish between outputs. In another embodiment, the machine learning results in a parameterization of the learned prediction model that may be used as the map.

Figure 3A:
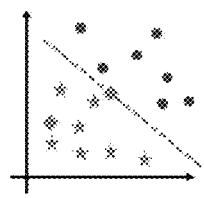
FIGS. 3A-D illustrate different approaches for determining an amount of training relative to a current sample where different types of predication models are used.
Figure 3B:
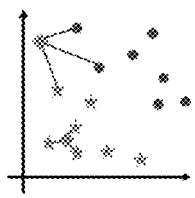
Figure 3C:
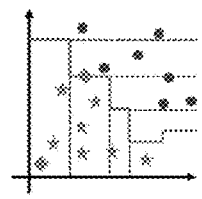
Figure 3D:
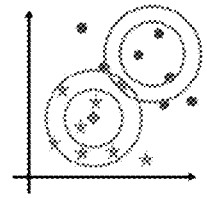

FIGS. 3A-D show example mappings of the decision functions. FIG. 3A shows a dashed line representing the distinction between the binary ground truth in the two-feature space. This line may be curved. In an N-dimensional space, the line may be a curved or other surface learned through training. This representation may be used for support vector machines or neural networks. FIG. 3B shows a decision function from k-means clustering. The clusters are labeled, as represented by the ground truth. FIG. 3C shows a decision function for a decision tree. A variety of lines, curves, and/or surfaces represent various parts of the decision function. FIG. 3D shows a decision function for a Bayes model. The nested circles represent different amounts of standard deviation from learned distributions. Other representations of the decision function may be used for the same or other types of machine learning.

The processor maps an input for a current sample not in the training data in the feature space. The current case is mapped in the same parameter space but without the ground truth. FIGS. 3A-D each show two examples. In this simplified feature space with a binary ground truth and only two features, the two examples of current input feature vectors are shown as diamonds. The mapping of these current samples is shown in the mapping of the training data of FIG. 2 (i.e., FIGS. 3A-D show the same mapping of training data as FIG. 2).

In act 16, the processor determines a metric of a distance in the feature space of the input for the current sample from the training data. The metric of the distance represents the relative position of the current sample to the training data and/or decision function. The distance is a conceptual or actual distance. For example, a Euclidian distance is determined. As another example, the distance is represented by a density of the training data samples and/or decision function in a region around the current sample. In yet another embodiment, the metric of distance is a count of the training samples within a predetermined region (defined by range in feature space or a percentage of the dynamic range of the features space) around the current sample. The relative position of the current sample indicates the amount of training.

The distance is for a subset of the input features for the patient and the training data. For example, the M closest samples to the current sample are identified. FIG. 3B shows identifying the three closest. M may be any integer, such as 3 or greater. The subset may be for a region, such as a circle or other shape centered on the current sample. The training data samples and/or parts of the decision function within the region are used to determine the distance. In alternative embodiments, the distance is for the entire features space, such as an average distance or average density of a region relative to the average density for the entire space or for another region.

The relative placement (e.g., metric of distance) may use the samples of training data without the ground truth. The distance is measured of the current sample to the samples of the training data regardless of the ground truth label. In other embodiments, the metric of distance is a function of the ground truth. For example, the ground truth of the closest samples weights the calculation. In a Euclidean distance with a binary ground truth, one ground truth may be negative and the other positive. The average of the actual distance reflects the ground truth. Where all the M closest samples are of a same ground truth, then the distance is minimal. Where the M closest samples include both of the binary ground truth, then the distance is closer to the threshold of minimal confidence. The ground truth label may be used as a weight, providing weighted distances compared to a predined confidence threshold. Where the ground truth is continuous over a range (e.g., not binary), then the weighting may likewise linearly map to different weights (e.g., magnitude of the weights changes instead of or in addition to negative and positive). In other embodiments, a separate metric of the distance uses the ground truth. The variance or other statistical measure of the ground truth for the local (e.g., within a region) samples of the training data indicates the amount of training data. A greater variance may indicate an insufficient amount of training data as the boundary may be less clear.

The relative position or metric or distance of the current sample to neighboring training samples is a measure of how well the prediction model is trained with respect to the current sample. A less direct measure of how well the prediction model is trained with respect to the current sample is the relative position or metric of distance from the decision function resulting from the training with the training data.

Where the distance or relative position of the current sample is from the decision function, then the actual distances to a closest part of the decision function is used. A measure of regional or local density may be used, such as a length or number of locations of the decision function within the region.

FIGS. 3A-D show the current samples relative to the samples of the training data. The metric of distance is based on the relative position, actual distance, density, and/or other function between the current sample and the training data without using the decision function.

FIGS. 3A-D also show the current samples relative to the decision functions. Depending on the underlying algorithm, retrieval of the confidence metric may be different using the decision function. FIG. 3A shows one example where the machine-learned network is a support vector machine or neural network. The relative position is determined as a distance to the decision function of the support vector machine or neural network (i.e., dotted line). Support vector machines and neural networks aim to determine a decision function (mostly a straight line for support vector machines and more complicated location by location mapping for neural networks). In these cases, the metric emphasizes the distance to the decision function. In FIG. 3A, one current sample is on the decision function, so represents a low confidence in the amount of training. The other current sample is farther away, so represents a higher confidence in the amount of training.

FIG. 3B shows one example where the machine-learned network is trained with k-means clustering. The relative position is determined as a distance to a number, M (e.g., M=3), of closest values for the training data. K-means clustering relies on the distance to a certain number of closest training data points. A large average distance represents a low confidence in the amount of training data, and a short average distance represents a high confidence. The current sample in the upper left is in a less dense region, so has a longer metric of distance. The current sample in the lower left is in a denser region, so has a shorter metric of distance.

FIG. 3C shows one example where the machine-learned network is a decision tree. The relative position is determined as a distance to the decision function of the decision tree. The distance to the closest piece-wise straight section of the decision tree is found. Decision trees build a decision function having of piece-wise straight sections. Current samples further away from decision function represent higher confidence (e.g., see the current sample in the lower left). Current samples closer to the decision function represent lower confidence (e.g., see the current sample on a segment of the decision function).

FIG. 3D shows one example where the machine-learned network is a Bayesian model. The relative position is determined as a distance to the decision function of the Bayesian model. Bayes' models are based on probability distributions. A current sample in an epicenter of a distribution function represents a high confidence in the amount of training (e.g., current sample near the center of the lower-left distribution). A current sample in locations where functions overlap and/or spaced from the distributions represents a lower confidence (e.g., current sample in the overlap).

Other metrics of the distance or relative position of the current sample to the training data may be used. Any metrics pertaining to the distance of the current input to training data points, the distance to the decision function, and/or the amount of wrongly categorized training data due to the decision function may be used. In training, the decision function may not classify all training samples into their ground truth category. This may occur due to variation in the samples where the machine training does not have the capability to adjust for the variation. Misclassification may be purposeful, such as where the samples are noisy and the training avoids accounting for outliers. The number of misclassified training samples in a region around the current sample indicates the amount of wrongly categorized training data relative to the current sample. The total number for all the training samples may be used. Other functions than a count may be used, such as a local density, ratio of misclassified to classified, or Euclidean distance to the closest misclassified samples.

The metric may be calculated directly, such as an average Euclidian distance or a regional distance. In other embodiments, the amount of training is determined as a function of the distance. The distances (e.g., actual distance or density) is a variable in a function for the metric. Any function may be used, such as applying a weight or having another variable based on a global confidence output by the prediction model.

In act 17, the processor thresholds the relative position. The metric of distance representing the relative position of the current sample to the training data is compared to a threshold or thresholds. The thresholds are predetermined values representing a level of confidence. For example, values of the metric representing lower confidence are distinguished from values of the metric representing higher confidence. The metric is compared with the predefined threshold so that a level of warning may be determined. If the metric is below a confidence threshold, then a warning to the user of the lower confidence in the amount of training relative to the current sample is generated. The metric may have an inverse relationship to confidence, so a warning is generated in the metric is above a metric threshold.

In act 18, the processor generates an image. The image includes the output of the machine-learned network. For example, an image of anatomy from the scan is output with one or more graphics for a detection, segmentation, or other clinical finding output from the prediction model. In another example, the part of the patient included in the image is based on the output from the prediction model, such as outputting an image of a segmented organ. In other examples, the output is alphanumeric text indicating a recommendation, risk, measurement, or other information. This information may be part of a report or a separate image with or without an image representation of the patient.

The image also includes the amount of training relative to the current sample for the patient. For example, the metric is used as the amount of training for the machine-learned prediction model trained with the training data. The amount of training with respect to the current sample of the input feature vector is output as the metric. The value of the metric and/or a coding (e.g., value relative to one or more thresholds) of color, graphic, or other indication is output. This output indicates to the user the relative position of the current sample to the training data. The user may use the information to determine how much to rely on the output from the prediction model. This assists in diagnosis, prognosis, and/or treatment.

The image may include a global confidence. For example, a percentage or color based on percentage is output to indicate a global confidence, which the prediction model was trained to output. The amount of training relative to the current sample (e.g., the metric of distance) may be one confidence value and the global confidence may be another confidence value. These different confidence values are output together on a same image or separately on different images.

The generated image is mapped to color or grayscale and loaded onto a display plane or buffer. The image is read out from the display plane to a display screen. The image may be output on any user interface, such as a monitor, tablet, smartphone, smart watch, or projector. The user interface displays the metric to the user.

In one embodiment, the image on user interface indicates the metric as a confidence bar, traffic light, in digits (e.g., alphanumerically), with a thumbs up or thumbs down (or other binary indication), or other graphic indicating the amount of relative training. The indication of the metric may be an annotation on an image of anatomy and/or color or other modulation of the output of the prediction model and/or the image of anatomy. In one embodiment, the amount of relative training is displayed as a warning. For example, the relative position of the current sample to the training data is thresholded. If the confidence is below a confidence threshold or the distance is above a distance threshold, then a warning is output. Any warning may be used, such as the binary indication, traffic light, indication of the threshold relative to the confidence bar, flashing or coloring the output of the prediction model, or a message.

The processor may output a recommendation in the same or different image with the amount of training. The amount of training is used to select a recommendation, such as using the results of the thresholding in act 17 to determine the recommendation. Different recommendations may be made for different amounts of training relative to the current sample and/or different situations. Example recommendations for low confidence (e.g., high distance) may include use of an additional post-processing algorithm, acquisition of additional images with a different modality, performing additional lab tests, and/or acquisition of additional images with the same modality but different scan and/or reconstruction parameters (e.g. for CT, using different pitch, mAs, kV, injection rate, contrast concentration, rotation time, kernel, slice thickness, etc.). The acquisition of additional images with the same modality may improve certain characteristics such as spatial resolution, spectral resolution, artifact reduction, temporal resolution, etc.

FIG. 4 shows a block diagram of one embodiment of a system for characterizing an amount of training of a machine-learned prediction model relative to an input sample. The amount of training relative to the input sample (e.g., values of features of the input feature vector) is determined by comparison to the training data, a decision function of the prediction model, and/or a relative amount of wrongly categorized training data.

The system includes one or more medical imagers 42, a processor 44, a memory 47 (e.g., a medical records database), and a display 48. Additional, different, or fewer components may be provided. For example, a user interface or input device is provided on the medical imager 42 and/or for the processor 44. In another example, a network or network connection is provided, such as for networking different components (e.g., medical imager 42 with the processor 44 and/or the processor 44 with the memory 47).

The memory 47, processor 44, and/or display 48 are part of a server, workstation, or computer. In one embodiment, the memory 47, processor 44, and/or display 48 are a server or workstation. The memory 47 may be part of a separate computer from the processor 44, such as being in a cloud hosted electronic health record or electronic medical records system. The medical imager 42 and the processor 44 are at different facilities, such as being remote from each other, or at a same facility.

The medical imager 42 is a magnetic resonance (MR), computed tomography (CT), x-ray, ultrasound, or nuclear medicine (e.g., positron emission tomography or single photon computed tomography) or another scanner. In other embodiments, the medical imager 42 is a multi-modality device, such as a combination of nuclear medicine and x-ray or CT. In yet other embodiments, invasive, other non-invasive, or minimally invasive imaging systems are used.

The medical imager 42 is configured to scan a patient. The same imager 42 may be used to scan different patients at different times. Other imagers 42 may be used to scan other patients. The medical imager 42 is configured to output scan data to the processor 44. The scan data is data resulting from the scan at any stage of processing. For example, data without reconstruction is provided. For CT, the data may be detector measurements for a plurality of projections without reconstruction into values for specific spatial locations. For MR, the data may be k-space data prior to Fourier transform to determine values for specific spatial locations. For nuclear imaging, the data may be line-of-response values prior to tomography to assign specific spatial locations. As another example, data after reconstruction is provided. Filtering, detection, scan conversion, and/or other image processing may or may not be applied to the data for communication to the processor 44. The medical imager 42 provides image data (e.g., scan data) as data resulting from scanning with any amount of processing towards generating an image. The image data may be formatted for display, such as RGB values, or may be in a scan format (e.g., scalar values).

The memory 47 is a random-access memory, system memory, cache memory, hard drive, optical media, magnetic media, flash drive, buffer, database, combinations thereof, or other now known or later developed memory device for storing training data (e.g., values for parameters or features) with or without ground truth, values for an input feature or parameter vector for a given patient, one or more thresholds, and/or a machine-learned prediction model or network 45. The memory 47 is part of the computer associated with the processor 44 or the medical imager 42 or is a separate or remote database for access over a computer network.

The memory 47 or other memory is alternatively or additionally a non-transitory computer readable storage medium storing data representing instructions executable by the programmed processor 44 and/or medical imager 42. The instructions for implementing the processes, methods, and/or techniques discussed herein are provided on non-transitory computer-readable storage media or memories, such as a cache, buffer, RAM, removable media, hard drive, or other computer readable storage media. Non-transitory computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone, or in combination. Likewise, processing strategies may include multiprocessing, multitasking, parallel processing, and the like.

In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU, tensor processing unit (TPU), neural processing unit, AI accelerator, or system.

The processor 44 is a general processor, control processor, digital signal processor, application specific integrated circuit, field programmable gate array, or other hardware processor for applying the machine-learned network 45 and/or determining an amount of training relative to an input sample. In one embodiment, the processor 44 is part of a computer, workstation, server, or other device configured to apply image processing and/or derive findings specific to patient. The processor 44 may be a network of computing devices, such as multiple computers or servers. The processor 44 is configured by software, hardware, and/or firmware.

The processor 44 is configured to output from the machine-learned prediction model. An input sample of values for parameters for the machine-learned network 45 is input to the machine-learned network 45. In response to the input of the input sample for a given patient, the machine-learned network 45 generates an output as trained. The output may be a detection, segmentation, measurement, recommendation, diagnosis, prognosis, or other clinical finding. The output may be or be based on a probability of confidence (e.g., global confidence). The prediction model outputs the probability.

The processor 44 is configured to determine an amount of training of the machine-learned prediction model. In addition to using the machine-learned network 45, the processor 44 also compares the current input sample to the training data that was used to train the machine-learned network 45. The values for the parameters for the input sample are compared to the values for the parameters of the training data and/or to a decision function of the machine-learned prediction model. Another comparison is of the values for the input sample to values of wrongly categorized training data. A relative position in a feature space is used for the comparison. The map 46 is of the training data, decision function, and/or wrongly categorized training samples. The map is in a feature space, such as locations defined by values of features. The values for a current patient are used to identify information from the map 46. The identified information indicates the amount of the training. A distance of the values for the current patient from the map content (e.g., from the values of the training data) for all or a sub-set of the features is found. The distance is a vector difference between map locations, a neighborhood density relative to the current values for the patient, a number of mapped locations in a neighborhood of the current values, and/or other metric.

The display 48 is a monitor, LCD, projector, plasma display, CRT, printer, or other now known or later developed device for displaying an image of the amount of the training of the machine-learned prediction model relative to the input sample. The amount of relative training may be displayed with other information, such as an output or information derived from the output of the machine-learned network 45. The amount may be indicated along with an image of anatomy.

The display 48 receives the output from the processor 44, medical imaging scanner 42, or memory 47. The processor 44 formats the data for display (e.g., mapping to RGB values) and stores the image in a buffer, configuring the display 48. The display 48 uses the image in the buffer to generate an image for viewing. The image includes graphics, alphanumeric text, anatomical scan, and/or other information. The display 48 is at the medical imager 42, the processor 44, a physician's computer, or another location.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for characterizing an amount of training in a medical system, the method comprising:
   scanning, by a medical imaging scanner, a patient;
   applying values for input features of a machine-learned network to the machine-learned network, the values being for the patient, at least one of the values being from the scanning, the applying resulting in an output by the machine-learned network;
   determining a relative position of the values for the input features of the patient to (a) values of the input features for training data used to train the machine-learned network and/or (b) a decision function of the machine-learned network; and
   displaying an image of the output by the machine-learned network and the amount of training relative to the values for the patient, the amount of training being a function of the relative position.

2. The method of claim 1 wherein determining the relative position comprises determining a distance.

3. The method of claim 1 wherein determining the relative position comprises determining a density.

4. The method of claim 1 wherein determining comprises determining the relative position to the values of the input features for the training data.

5. The method of claim 1 wherein determining comprises determining the relative position to decision function.

6. The method of claim 1 further comprising determining an amount of wrongly categorized training data of the training data due to the decision function relative to the values for the input features of the patient.

7. The method of claim 1 wherein displaying comprises displaying the amount of the training as a first confidence and displaying a global confidence provided by the machine-learned network with or as the output.

8. The method of claim 1 wherein displaying comprises displaying the amount of the training on a confidence bar, as a traffic light, as a binary indication of acceptance, or alphanumerically.

9. The method of claim 1 further comprising thresholding the relative position, wherein displaying comprises displaying the amount as a warning where the relative position is above a threshold.

10. The method of claim 1 wherein the machine-learned network is a support vector machine or neural network, wherein determining comprises determining the relative position as a distance to the decision function of the support vector machine or neural network, the decision function being a line or surface.

11. The method of claim 1 wherein the machine-learned network is a k-means clustering, wherein determining comprises determining the relative position as a distance to a number of closest values for the training data.

12. The method of claim 1 wherein the machine-learned network is a decision tree, wherein determining comprises determining the relative position as a distance to the decision function of the decision tree, the decision function of the decision tree being piece-wise straight sections.

13. The method of claim 1 wherein the machine-learned network is a Bayesian model, wherein determining comprises determining the relative position as a distance to the decision function of the Bayesian model, the decision function comprising probability distributions.

14. The method of claim 1 wherein determining comprises determining for a subset of the input features for the patient and the training data.

15. The method of claim 1 wherein determining the relative position comprises determining a metric indicative of how well the machine-learned network was trained relative to the input features for the patient, the metric determined separately from the output of the machine-learned network.

* * * * *